United States Patent
Sherman

(10) Patent No.: US 6,914,141 B2
(45) Date of Patent: Jul. 5, 2005

(54) CLOPIDOGREL BISULFATE TABLET FORMULATION

(76) Inventor: Bernard Charles Sherman, 50 Old Colony Road, Toronto, Ontario (CA), M2L 2K1

( * ) Notice: Subject to any disclaimer, the term of this patent is extended or adjusted under 35 U.S.C. 154(b) by 130 days.

(21) Appl. No.: 10/286,810

(22) Filed: Nov. 4, 2002

(65) Prior Publication Data

US 2003/0096837 A1 May 22, 2003

(30) Foreign Application Priority Data

Nov. 9, 2001 (CA) ................................................ 2363053

(51) Int. Cl.[7] ........................ A61K 31/47; C07D 515/02
(52) U.S. Cl. ........................ 546/114; 514/39; 514/301; 424/408; 424/464; 424/468; 424/474
(58) Field of Search ................................ 424/464, 408, 424/468, 474; 546/114; 514/39, 301

(56) References Cited

U.S. PATENT DOCUMENTS

| | | | |
|---|---|---|---|
| 4,847,265 A | | 7/1989 | Badorc et al. |
| 6,210,712 B1 | * | 4/2001 | Edgren et al. ............... 424/473 |
| 6,504,030 B1 | * | 1/2003 | Bousquet et al. ........... 546/114 |
| 6,635,763 B2 | * | 10/2003 | Pandey et al. ............... 546/114 |
| 6,737,411 B2 | * | 5/2004 | Valeriano et al. .............. 514/39 |
| 6,737,419 B2 | * | 5/2004 | Sherman ................ 514/212.07 |
| 6,767,913 B2 | * | 7/2004 | Lifshitz et al. ............. 514/301 |
| 6,800,759 B2 | * | 10/2004 | Valeriano et al. ........... 546/114 |

OTHER PUBLICATIONS

Abstract of WO 9961026 A1 (Batra et al), AN: 1999:763873 HCAPLUS, DN: 132:15626.*

* cited by examiner

*Primary Examiner*—Sabiha N. Qazi
(74) *Attorney, Agent, or Firm*—Nixon & Vanderhye P.C.

(57) ABSTRACT

Pharmaceutical tablets comprising clopidogrel bisulfate and a lubricant selected from zinc stearate, stearic acid, and sodium stearyl fumarate.

10 Claims, No Drawings

CLOPIDOGREL BISULFATE TABLET FORMULATION

BACKGROUND OF THE INVENTION

Clopidogrel is a compound disclosed in U.S. Pat. No. 4,847,265 to be therapeutically useful as an inhibitor of platelet agglomeration.

Tablets containing clopidogrel as clopidogrel bisulfate are sold in the United States and elsewhere under the tradename Plavix™.

According to the labelling of Plavix™, each tablet contains 98 mg of clopidogrel bisulfate, which is the molar equivalent of 75 mg of clopidogrel. The tablets are made as cores which are then film coated. The cores comprise, in addition to the clopidogrel bisulfate, the following inactive ingredients: lactose, hydrogenated castor oil, microcrystalline cellulose, polyethylene glycol 6000 and pregelatinized starch. The weight of each tablet is about 240 mg.

Lactose and microcrystalline cellulose are ingredients that are commonly used as fillers and binders. Starch is commonly used as a disintegrant to cause the tablets to disintegrate in gastrointestinal fluid. Hydrogenated castor oil and polyethylene glycol are sometimes, although rarely, used as lubricants.

In the manufacture of tablets, it is generally necessary to include a lubricant in the mix of ingredients to prevent sticking of the compressed tablets to the punches, and also to prevent binding between the punches and the dies.

The most commonly used lubricant is magnesium stearate. U.S. Pat. No. 4,847,265, in examples 1 and 2, shows the use of magnesium stearate as the lubricant.

It is thus unusual that Plavix™ tablets do not contain magnesium stearate as the lubricant, but instead contain hydrogenated castor oil and polyethylene glycol as lubricants. Both of these ingredients have occasionally been used as lubricants, but they are not as effective as magnesium stearate, and their use in place of magnesium stearate must be expected to make it difficult to produce tablets at high speed without experiencing sticking to the punches or binding between the punches and dies. It appears that the reason that magnesium stearate is not used in Plavix™ tablets is that there is an interaction between clopidogrel bisulfate and magnesium stearate that causes degradation of the clopidogrel bisulfate, so that the stability of clopidogrel sulfate tablets which include magnesium stearate as lubricant is insufficient to enable sale of such tablets.

In light of this prior art, the object of the present invention is to provide stable clopidogrel hydrochloride tablets that contain a lubricant that is more effective than hydrogenated castor oil and polyethylene glycol 6000.

BRIEF SUMMARY OF THE INVENTION

It has surprisingly been found that clopidogrel bisulfate tablets, comprising a lubricant selected from the group consisting of zinc stearate, stearic acid, and sodium stearyl fumarate, are much more stable than tablets comprising either magnesium stearate or calcium stearate as lubricant. Zinc stearate, stearic acid and sodium stearyl fumarate are also more effective lubricants than either hydrogenated castor oil or polyethylene glycol 6000. The invention is thus pharmaceutical tablets comprising clopidogrel bisulfate and a lubricant selected from zinc stearate, stearic acid and sodium stearyl fumarate.

DETAILED DESCRIPTION OF THE INVENTION

Pharmaceutical tablets comprising clopidogrel bisulfate will generally contain, in addition to the active ingredient, one or more ingredients that serve as fillers and binders such as, for example, lactose, microcrystalline cellulose, or methylcellulose. It has also surprisingly been found that microcrystalline cellulose inhibits dissolution of clopidogrel bisulfate, so that the tablets will preferably exclude microcrystalline cellulose. The tablets will preferably comprise lactose or methylcellulose.

The tablets will further comprise at least one ingredient as a lubricant to avoid sticking to the tooling in the tabletting process. As aforesaid, it has been found that improved stability is achieved by selecting the lubricant from zinc stearate, stearic acid and sodium stearyl fumarate.

When the lubricant is zinc stearate or sodium stearyl fumarate, the amount will preferably be from about 0.5% to about 3% of the weight of the tablet. When the lubricant is stearic acid, the amount will preferably be from about 1% to about 6% of the weight of the tablet.

Clopidogrel bisulfate tablets will preferably further comprise a disintegrant to cause the tablets to swell and disintegrate in gastrointestinal fluid after ingestion. As aforesaid, Plavix™ tablets comprise starch which serves as a disintegrant, but is desirable to use a more efficient disintegrant; i.e. one that is effective in a smaller quantity. Preferred disintegrants are croscarmellose sodium, sodium starch glycolate, and crospovidone.

The amount of disintegrant will preferably be from about 0.5% to about 10% of the weight of the tablet.

The tablets of this invention will optionally also comprise other ingredients, such as, for example, colloidal silicon dioxide as a glidant.

The tablets will also optionally be coated with a film coat.

The clopidogrel bisulfate tablets of this invention can be prepared by conventional tablet forming techniques such as, for example, wet granulation and dry granulation. In the wet granulation process, the active ingredient is mixed with some or all of the filler. This blend is then wet granulated with water or an organic solvent, optionally containing a binder in solution. The resultant wet granulation is then dried and milled. The granules are then mixed with the remaining ingredients, which will include the lubricant, to produce the final mix, which is then compressed into tablets.

In the dry granulation process, the active ingredient is mixed with the other ingredients without addition of any solvent, and thus without the need for drying. Again the final mix is compressed into tablets. The dry granulation approach is preferred as it is simpler and thus less costly.

The invention will be further understood from the following examples:

|  | Example No.: | | | | |
| --- | --- | --- | --- | --- | --- |
|  | 1 | 2 | 3 | 4 | 5 |
| Clopidogrel Bisulfate | 98.0 | 98.0 | 98.0 | 98.0 | 98.0 |
| Anhydrous Lactose | 49.0 | 49.0 | 49.0 | 49.0 | 49.0 |
| Methylcellulose 15CPS | 17.0 | 17.0 | 17.0 | 17.0 | 17.0 |
| Crospovidone | 12.0 | 12.0 | 12.0 | 12.0 | 12.0 |
| Magnesium Stearate | 3.8 | X | X | X | X |
| Calcium Stearate | X | 3.8 | X | X | X |
| Zinc Stearate | X | X | 3.8 | X | X |
| Sodium Stearyl Fumarate | X | X | X | 3.8 | X |
| Stearic Acid | X | X | X | X | 8.8 |
| Colloidal Silicon Dioxide | 0.2 | 0.2 | 0.2 | 0.2 | 0.2 |
|  | 180. | 180. | 180. | 180. | 185. |

For each of the 5 examples, the ingredients in the proportions listed were mixed together. The powder mixture was then compressed into tablets of weight 180 mg for examples 1 to 4, and 185 mg for example 5. Because stearic acid is not as efficient a lubricant as the lubricants of the other examples, a larger quantity of lubricant was used in example 5 than in examples 1 to 4.

Sample tablets from each example were stored at 60° C. for 2 weeks and then tested by an HPLC method to determine degradation products as a percentage of the initial clopidogrel bisulfate content.

The results were as follows:

| Example No: | 1 | 2 | 3 | 4 | 5 |
|---|---|---|---|---|---|
| Total Degradation Products | 3.8% | 3.8% | 1.3% | 1.0% | 1.2% |

It thus can be seen that, when any of zinc stearate, sodium stearyl fumarate or stearic acid is used as lubricant, the degradation rate is substantially less than when either magnesium stearate or calcium stearate is used.

What is claimed is:

1. A pharmaceutical tablet which comprises clopidogrel bisulfate and a lubricant selected from the group consisting of zinc stearate, sodium stearyl fumarate and stearic acid.
2. A table of claim 1 which comprises zinc stearate.
3. A tablet of claim 1 which comprises sodium stearyl fumarate.
4. A tablet of claim 1 which comprises stearic acid.
5. A pharmceutical tablet which comprises clopidogrel bisulfate and a lubricant selected from the group consisting of zinc stearate, sodium stearyl fumarate and stearic acid, wherein said tablet does not comprise microcrystalline cellulose.
6. A tablet of claim 1 which comprises lactose.
7. A tablet of claim 1 which comprises methylcellulose.
8. A tablet of claim 1 which comprises crospovidone.
9. A tablet of claim 1 which comprises croscarmellose sodium.
10. A tablet of claim 1 which comprises sodium starch glycolate.

* * * * *